(12) United States Patent  (10) Patent No.: US 8,022,213 B2
Bissantz et al.  (45) Date of Patent: *Sep. 20, 2011

(54) SPIRO-PIPERIDINE DERIVATIVES

(75) Inventors: Caterina Bissantz, Village Neuf (FR); Christophe Grundschober, Rodersdorf (CH); Raffaello Masciadri, Basel (CH); Hasane Ratni, Habsheim (FR); Mark Rogers-Evans, Oberwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 963 days.

This patent is subject to a terminal disclaimer.

(21) Appl. No.: 11/947,836

(22) Filed: Nov. 30, 2007

(65) Prior Publication Data

US 2008/0161299 A1 Jul. 3, 2008

(30) Foreign Application Priority Data

Dec. 7, 2006 (EP) .................................. 06125645

(51) Int. Cl.
C07D 401/04 (2006.01)
A61K 31/438 (2006.01)

(52) U.S. Cl. .......................................... 546/18; 514/278
(58) Field of Classification Search .............. 546/18; 514/278

See application file for complete search history.

(56) References Cited

U.S. PATENT DOCUMENTS 7,351,706 B2 * 4/2008 Bissantz et al. ........... 514/230.5

FOREIGN PATENT DOCUMENTS

| WO | WO 00/14067 | 3/2000 |
| WO | WO 01/85725 | 11/2001 |
| WO | WO 2004/035549 | 4/2004 |
| WO | WO 2007/077122 | 7/2007 |

OTHER PUBLICATIONS

Ebner et al., (2002), Eur. J. Neurosci. vol. 15 pp. 384-388.
Bielsky et al., (2004), Neuropsychopharmacology, vol. 29 pp. 483-493.
Michelini et al., (1999), Annals NY Acad. Sci. vol. 897 pp. 198-211.
Van Kerckhoven et al., (2002) Eur. J. Pharmacol. vol. 449 pp. 135-141.
Liebsch et al., (1995), Regulatory Peptides vol. 59 pp. 229-239.
Clark, R. et al, *Jour of Med. Chem*. (1983) XP002432972.
Clark, R. et al, *Jour of Med. Chem*. (1995) XP000941460.

* cited by examiner

*Primary Examiner* — Rita Desai
(74) *Attorney, Agent, or Firm* — George W. Johnston; Patricia S. Rocha-Tramaloni; Kimberly J. Prior

(57) ABSTRACT

Present invention is concerned with novel indol-2-yl-carbonyl-spiro-piperidine derivatives as V1a receptor antagonists, their manufacture, pharmaceutical compositions containing them. The active compounds of the present invention are useful in the treatment of anxiety and depressive disorders and other diseases. The compounds of present invention have the general formula (I)

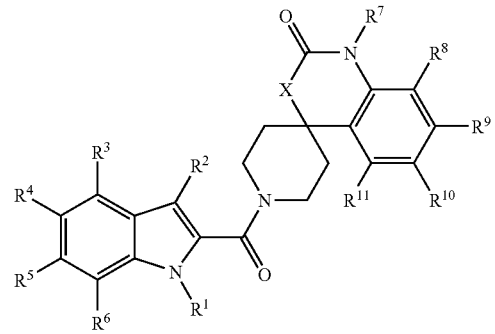

wherein $R^1$ to $R^{11}$ and X are as defined in the description.

23 Claims, No Drawings

SPIRO-PIPERIDINE DERIVATIVES

PRIORITY TO RELATED APPLICATION(S)

This application claims the benefit of European Patent Application No. 06125645.9, filed Dec. 7, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann NY Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41)

SUMMARY OF THE INVENTION

The present invention provides novel indol-2-yl-carbonyl-spiro-piperidine derivatives as V1a receptor antagonists, their manufacture, pharmaceutical compositions containing them and their use for the treatment of anxiety and depressive disorders and other diseases.

In particular, the present invention provides compounds of formula (I)

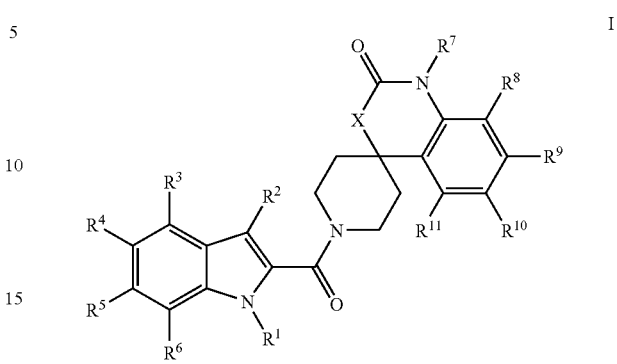

wherein
X is O or $CH_2$;
$R^1$ is hydrogen,
  $C_{1-6}$-alkyl, optionally substituted by CN or OH. or
  —($C_{1-6}$-alkylene)-C(O)—$NR^aR^b$;
$R^2$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-C(O)$R^f$,
  benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
  halo, or
  $C_{1-6}$-alkyl;
$R^4$ is hydrogen,
  halo,
  $C_{1-6}$-alkyl,
  halo-$C_{1-6}$-alkyl,
  $C_{1-6}$-alkoxy,
  halo-$C_{1-6}$-alkoxy, or
  —O—$C_{2-10}$-alkenyl;
$R^5$ is hydrogen,
  halo,
  $C_{1-6}$-alkyl, or
  $C_{1-6}$-alkoxy;
or $R^4$ and $R^5$ are bound together to form a ring with the benzo moiety, wherein
  —$R^4$—$R^5$— is —O—$(CH_2)_n$—O— wherein n is 1 or 2;
$R^6$ is hydrogen,
  $C_{1-6}$-alkyl, optionally substituted by CN or OH,
  —($C_{1-6}$-alkylene)-$NR^gR^h$,
  —($C_{1-6}$-alkylene)-C(O)—$NR^iR^j$,
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-C(O)$R^f$,
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  —($C_{1-3}$-alkylene)-$R^m$, wherein $R^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

or $R^5$ and $R^6$ are bound together to form a ring with the benzo moiety, wherein
—$R^5$—$R^6$ is —O—$(CH_2)_n$—C(O)—,
—C(O)—$(CH_2)_n$—O—, or
—O—$(CH_2)_n$—O— wherein n is 1 or 2;

$R^7$ is hydrogen or $C_{1-6}$-alkyl;

$R^8$, $R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$ alkoxy;

$R^a$, $R^b$, $R^i$ and $R^j$ are each independently
hydrogen,
$C_{1-6}$-alkyl,
—($C_{1-6}$-alkylene)-$NR^kR^l$;
wherein $R^k$ and $R^l$ are each independently hydrogen or $C_{1-6}$-alkyl,
or $R^a$ and $R^b$, or $R^i$ and $R^j$ together with the nitrogen to which they are bound form a five or six membered heterocycle comprising one or two heteroatoms selected from the group of nitrogen, oxygen and sulfur;

$R^c$, $R^d$, $R^g$ and $R^h$ are each independently
hydrogen,
$C_{1-6}$-alkyl,
—C(O)$R^e$, or —S(O)$_2R^e$,
wherein $R^e$ is selected from
hydrogen,
$C_{1-6}$-alkyl, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
$R^c$ and $R^d$, or $R^g$ and $R^h$ together with the nitrogen to which they are bound form a five or six membered heterocycle comprising one or two heteroatoms selected from the group of nitrogen, oxygen and sulfur, or
$R^c$ and $R^d$, or $R^g$ and $R^h$ together with the nitrogen to which they are bound form isoindole-1,3-dione;

$R^f$ is selected from
hydrogen,
$C_{1-6}$-alkyl,
$C_{1-6}$-alkoxy; and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

or a pharmaceutically acceptable salt thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor.

The present invention provides compounds which act as V1a receptor modulators, and in particular as V1a receptor antagonists. Such antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

In the present description, the term "alkyl," alone or in combination with other groups, refers to a branched or straight-chain monovalent saturated hydrocarbon radical. The term "$C_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene" means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, and the like.

In the present description, the terms "alkoxy" and "$C_{1-6}$-alkoxy" refer to the group R'—O—, wherein R' is $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy.

In the present description, the terms "thioalkyl" and "$C_{1-6}$-thioalkyl" refer to the group R'—S—, wherein R' is $C_{1-6}$-alkyl as defined above.

The terms "$C_{1-6}$-hydroxyalkyl" and "$C_{1-6}$-alkyl substituted by OH" denote a $C_{1-6}$-alkyl group as defined above wherein at least one of the hydrogen atoms of the alkyl group is replaced by a hydroxyl group.

The terms "$C_{1-6}$-cyanoalkyl" and "$C_{1-6}$-alkyl substituted by CN" denote a $C_{1-6}$-alkyl group as defined above wherein at least one of the hydrogen atoms of the alkyl group is replaced by a CN group.

The terms "halo" or "halogen" refer to fluorine (F), chlorine (Cl), bromine (Br) and iodine (I) with fluorine, chlorine and bromine being preferred.

The term "halo-$C_{1-6}$-alkyl" denotes a $C_{1-6}$-alkyl group as defined above wherein at least one of the hydrogen atoms of the alkyl group is replaced by a halogen atom, preferably fluoro or chloro, most preferably fluoro. Examples of halo-$C_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-6}$-alkyl groups are difluoro- or trifluoro-methyl or -ethyl.

The term "halo-$C_{1-6}$-alkoxy" denotes a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl", alone or in combination, denotes a straight-chain or branched hydrocarbon residue of 2 to 12 carbon atoms comprising at least one double bond. A preferred sub-group of $C_{2-12}$-alkenyl is $C_{2-6}$-alkyenyl. Examples of the preferred alkenyl groups are ethenyl, propen-1-yl, propen-2-yl (allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "5 or 6 membered heteroaryl" means an aromatic ring of 5 or 6 ring atoms as ring members containing one, two, or three ring heteroatoms selected from N, O, or S, the rest being carbon atoms. 5 or 6 membered heteroaryl can optionally be substituted with one, two, three or four substituents, wherein each substituent may independently be selected from the group consisting of hydroxy, $C_{1-6}$-alkyl, $C_{1-6}$-alkoxy, $C_{1-6}$-thioalkyl, halo, cyano, nitro, halo-$C_{1-6}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, or carbonylamino, unless otherwise specifically indicated. Preferred substituents are halo, halo-$C_{1-6}$-alkyl, $C_{1-6}$-alkyl, $C_{1-6}$-alkoxy, halo-$C_{1-6}$-alkoxy, nitro, or cyano. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "heterocycloalkyl" means a monovalent saturated moiety, consisting of one ring of 3 to 7, preferably from 4 to 6 atoms as ring members, including one, two, or three heteroatoms chosen from nitrogen, oxygen or sulfur, the rest being carbon atoms. 3 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, cyano, nitro, halo-$C_{1-6}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, or carbonylamino, unless otherwise specifically indicated.

Preferred substituents are halo, halo-$C_{1-6}$-alkyl, $C_{1-6}$-alkyl, $C_{1-6}$-alkoxy, halo-$C_{1-6}$-alkoxy, nitro, or cyano. Examples of heterocyclic moieties include, but are not limited to, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein.

The term "heterocycle" in the definition "$R^a$ and $R^b$, $R^c$ and $R^d$, $R^g$ and $R^h$, $R^i$ and $R^j$, together with the nitrogen to which they are bound form a five- or six-membered heterocycle comprising one or two heteroatoms selected from the group of nitrogen, oxygen and sulfur" means either heterocycloalkyl or heteroaryl in the above-given sense, which may optionally be substituted as described above. Preferably, the "heterocycle" may optionally be substituted with one, two or three substituents selected from halo, halo-$C_{1-6}$-alkyl, $C_{1-6}$-alkyl, $C_{1-6}$-alkoxy, halo-$C_{1-6}$-alkoxy, nitro, or cyano. Preferred heterocycles are piperazine, N-methylpiperazine, morpholin, piperidine and pyrrolidine.

The term "one or more" substituents preferably means one, two or three substituents per ring.

The term "3- to 6-membered cycloalkyl" denotes a saturated or partially saturated ring containing from 3 to 6 carbon atoms, for example cyclopropyl, cyclopentyl, cyclopentenyl, cyclohexyl, or cyclohexenyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

In detail, the present invention relates to compounds of the general formula (I)

wherein
X is O or $CH_2$;
$R^1$ is hydrogen,
  $C_{1-6}$-alkyl, optionally substituted by CN or OH, or
  —($C_{1-6}$-alkylene)-C(O)—$NR^aR^b$;
$R^2$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-C(O)$R^f$,
  benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
  halo, or
  $C_{1-6}$-alkyl;
$R^4$ is hydrogen,
  halo,
  $C_{1-6}$-alkyl,
  halo-$C_{1-6}$-alkyl,
  $C_{1-6}$-alkoxy,
  halo-$C_{1-6}$-alkoxy, or
  —O—$C_{2-10}$-alkenyl;
$R^5$ is hydrogen,
  halo,
  $C_{1-6}$-alkyl, or
  $C_{1-6}$-alkoxy;
or $R^4$ and $R^5$ are bound together to form a ring with the benzo moiety, wherein
  —$R^4$—$R^5$— is —O—$(CH_2)_n$—O— wherein n is 1 or 2;
$R^6$ is hydrogen,
  $C_{1-6}$-alkyl, optionally substituted by CN or OH,
  —($C_{1-6}$-alkylene)-$NR^gR^h$,
  —($C_{1-6}$-alkylene)-C(O)—$NR^iR^j$, —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
nitro,
halo,
cyano,
$C_{1-6}$-alkoxy,
halo-$C_{1-6}$-alkoxy,
halo-$C_{1-6}$-alkyl,
—($C_{1-6}$-alkylene)-C(O)$R^f$,
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
—($C_{1-3}$-alkylene)-$R^m$,
wherein $R^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or $R^5$ and $R^6$ are bound together to form a ring with the benzo moiety, wherein
—$R^5$—$R^6$ is —O—$(CH_2)_n$—C(O)—,
—C(O)—$(CH_2)_n$—O—, or
—O—$(CH_2)_n$—O— wherein n is 1 or 2;
$R^7$ is hydrogen or $C_{1-6}$-alkyl;
$R^8$, $R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$ alkoxy;
$R^a$, $R^b$, $R^i$ and $R^j$ are each independently
hydrogen,
$C_{1-6}$-alkyl,
—($C_{1-6}$-alkylene)-$NR^kR^l$;
wherein $R^k$ and $R^l$ are each independently hydrogen or $C_{1-6}$-alkyl,
or $R^a$ and $R^b$, or $R^i$ and $R^j$ together with the nitrogen to which they are bound form a five or six membered heterocycle comprising one or two heteroatoms selected from the group of nitrogen, oxygen and sulfur;
$R^c$, $R^d$, $R^g$ and $R^h$ are each independently
hydrogen,
$C_{1-6}$-alkyl,
—C(O)$R^e$, or —S(O)$_2R^e$,
wherein $R^e$ is selected from
hydrogen,
$C_{1-6}$-alkyl, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
$R^c$ and $R^d$, or $R^g$ and $R^h$ together with the nitrogen to which they are bound form a five or six membered heterocycle comprising one or two heteroatoms selected from the group of nitrogen, oxygen or sulfur, or
$R^c$ and $R^d$, or $R^g$ and $R^h$ together with the nitrogen to which they are bound form isoindole-1,3-dione;
$R^f$ is selected from
hydrogen,
$C_{1-6}$-alkyl,
$C_{1-6}$-alkoxy; and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or a pharmaceutically acceptable salt thereof.

In certain embodiments of the invention, $R^a$ and $R^b$, $R^c$ and $R^d$, $R^i$ and $R^j$, or $R^g$ and $R^h$ together with the nitrogen to which they are bound may form piperazine, 4-($C_{1-6}$-alkyl)-piperazine, 4-methylpiperazine, morpholine, piperidine or pyrrolidine.

In certain embodiments of the invention, wherein $R^m$ is a 5- to 6-membered heteroaryl, the preferred heteroaryl is selected from the group consisting of pyridine, pyrimidine, pyrazine, pyridazine, imidazole, pyrazole, oxazole, and isoxazole.

In embodiments of the invention, wherein $R^m$ is a 4- to 6-membered heterocycloalkyl, the preferred heterocycloalkyl is selected from the group consisting of pyrrolidine, oxethane, tetrahydropyrane, piperidine, morpholine, and piperazine.

In certain embodiments of the invention, $R^1$ is hydrogen or $C_{1-6}$-alkyl, optionally substituted by CN or OH.

In certain embodiments of the invention,
$R^2$ is hydrogen,
$C_{1-6}$-alkyl,
$C_{1-6}$-alkoxy,
—($C_{1-6}$-alkylene)-$NR^cR^d$,
wherein $R^c$ and $R^d$ are each independently
hydrogen,
—C(O)$R^e$, or —S(O)$_2R^e$,
wherein $R^e$ is selected from
hydrogen,
$C_{1-6}$-alkyl, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
$R^c$ and $R^d$ together with the nitrogen to which they are bound form isoindole-1,3-dione;
—($C_{1-6}$-alkylene)-C(O)$R^f$,
wherein $R^f$ is selected from
hydrogen,
$C_{1-6}$-alkyl,
$C_{1-6}$-alkoxy, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
benzyl, optionally substituted by halo, halo-$C_{1-6}$-alkyl, $C_{1-6}$-alkyl, $C_{1-6}$-alkoxy, halo-$C_{1-6}$-alkoxy, nitro, or cyano, or
phenyl, optionally substituted by halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^2$ is hydrogen or $C_{1-6}$-alkyl.

In certain embodiments of the invention, $R^3$ is hydrogen.

In certain embodiments of the invention, $R^4$ is hydrogen, halo, $C_{1-6}$-alkyl, or $C_{1-6}$-alkoxy.

In certain embodiments of the invention,
$R^6$ is hydrogen,
$C_{1-6}$-alkyl, optionally substituted by CN or OH,
—($C_{1-6}$-alkylene)-$NR^gR^h$,
wherein $R^g$ and $R^h$ are each independently selected from hydrogen, and $C_{1-6}$-alkyl; or wherein
$R^g$ and $R^h$ together with the nitrogen to which they are bound form a five or six membered heterocycle comprising one or two heteroatoms selected from the group of nitrogen, oxygen and sulfur,
—($C_{1-6}$-alkylene)-C(O)—$NR^iR^j$,
wherein $R^i$ and $R^j$ are each independently
hydrogen,
$C_{1-6}$-alkyl,
—($C_{1-6}$-alkylene)-$NR^kR^l$,
wherein $R^k$ and $R^l$ are each independently hydrogen or $C_{1-6}$-alkyl,
or $R^i$ and $R^j$ together with the nitrogen to which they are bound form a five or six membered heterocycle comprising one or two heteroatoms selected from the
group of nitrogen, oxygen and sulfur,
—O-benzyl, optionally substituted by one or more halo,
halo-$C_{1-6}$-alkyl, $C_{1-6}$-alkyl, $C_{1-6}$-alkoxy, halo-$C_{1-6}$-alkoxy, nitro, or cyano,
nitro,
halo,
cyano,
$C_{1-6}$-alkoxy,
halo-$C_{1-6}$-alkoxy,
halo-$C_{1-6}$-alkyl,
—($C_{1-6}$-alkylene)-C(O)$R^f$,
$R^f$ is selected from
hydrogen,
$C_{1-6}$-alkyl,
$C_{1-6}$-alkoxy, or
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
—($C_{1-3}$-alkylene)-$R^m$,
wherein $R^m$ is phenyl, a 5- to 6-membered heteroaryl, 4- to 6-membered heterocycloalkyl or 3 to 6-membered cycloalkyl,
each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.
In certain embodiments of the invention,
$R^6$ is hydrogen,
$C_{1-6}$-alkyl, optionally substituted by CN or OH,
—($C_{1-6}$-alkylene)-$NR^gR^h$,
wherein $R^g$ and $R^h$ are each independently selected from hydrogen, and $C_{1-6}$-alkyl; or wherein
$R^g$ and $R^h$ together with the nitrogen to which they are bound form a five or six membered heterocycle comprising one or two heteroatoms selected from the group of nitrogen, oxygen and sulfur,
—($C_{1-6}$-alkylene)-C(O)—$NR^iR^j$,
wherein $R^i$ and $R^j$ are each independently
hydrogen,
$C_{1-6}$-alkyl,
—($C_{1-6}$-alkylene)-$NR^kR^l$,
wherein $R^k$ and $R^l$ are each independently hydrogen or $C_{1-6}$-alkyl,
or $R^i$ and $R^j$ together with the nitrogen to which they are bound form a five or six membered heterocycle comprising one or two heteroatoms selected from the group of nitrogen and oxygen.
In certain embodiments of the invention, $R^6$ is hydrogen or $C_{1-6}$-alkyl.
In certain embodiments of the invention, $R^7$ is hydrogen.
In certain embodiments all $R^8$ to $R^{11}$ are hydrogen.
In certain embodiments, $R^8$ to $R^{11}$ are independently hydrogen or halo.
In certain embodiments, $R^9$ is fluoro, and $R^8$, $R^{10}$ and $R^{11}$ are hydrogen.
In certain embodiments, $R^8$, $R^9$ and $R^{11}$ are hydrogen and $R^{10}$ is bromo.
In certain embodiments, $R^8$ to $R^{11}$ are independently hydrogen or methyl.
In certain embodiments, $R^8$ to $R^{10}$ are hydrogen and $R^{11}$ is methyl.
In certain embodiments of the invention, X is O, i.e. compounds of formula (Ia)

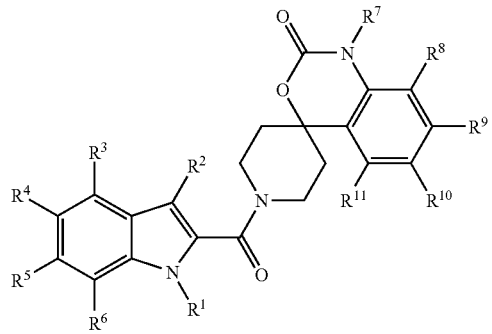

wherein $R^1$ to $R^{11}$ are as defined herein above.
In certain embodiments of the invention, X is $CH_2$, i.e. compounds of formula (Ib)

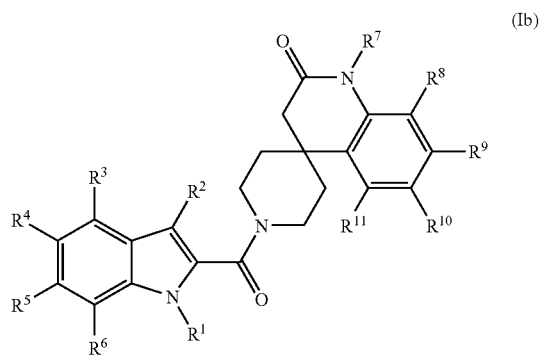

wherein $R^1$ to $R^{11}$ are as defined herein above.
In certain embodiments of the invention, $R^1$ to $R^6$ are not all hydrogen.
In certain embodiments of the invention, $R^1$ to $R^{11}$ are not all hydrogen.
The invention further encompasses an embodiment with the compound of formula (I), wherein
X is O or $CH_2$;
$R^1$ is hydrogen;
$C_{1-6}$-alkyl, optionally substituted by CN or OH;
—($C_{1-6}$-alkylene)-C(O)—$NR^aR^b$,
wherein $R^a$ and $R^b$ are each independently hydrogen or $C_{1-6}$-alkyl,
$R^2$ is hydrogen,
$C_{1-6}$-alkyl,
$C_{1-6}$-alkoxy,
—($C_{1-6}$-alkylene)-$NR^cR^d$,
wherein $R^c$ and $R^d$ are each independently
hydrogen,
—C(O)$R^e$, or —S(O)$_2R^e$,
wherein $R^e$ is selected from
hydrogen,
$C_{1-6}$-alkyl, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
$R^c$ and $R^d$ together with the nitrogen to which they are bound form isoindole-1,3-dione, —(C$_{1-6}$-alkylene)-C(O)R$^f$,
  wherein R$^f$ is selected from
    hydrogen,
    C$_{1-6}$-alkyl,
    C$_{1-6}$-alkoxy, and
    phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
  benzyl, optionally substituted by halo, halo-C$_{1-6}$-alkyl, C$_{1-6}$-alkyl, C$_{1-6}$-alkoxy, halo-C$_{1-6}$-alkoxy, nitro, or cyano or
  phenyl, optionally substituted by halo, halo-C$_{1-6}$-alkyl, C$_{1-6}$-alkyl, C$_{1-6}$-alkoxy, halo-C$_{1-6}$-alkoxy, nitro, or cyano;
R$^3$ is hydrogen,
  halo, or
  C$_{1-6}$-alkyl;
R$^4$ is hydrogen,
  halo,
  C$_{1-6}$-alkyl,
  halo-C$_{1-6}$-alkyl,
  C$_{1-6}$-alkoxy,
  halo-C$_{1-6}$-alkoxy, or
  —O—C$_{2-10}$-alkenyl;
R$^5$ is hydrogen,
  halo,
  C$_{1-6}$-alkyl, or
  C$_{1-6}$-alkoxy;
or R$^4$ and R$^5$ are bound together to form a ring with the benzo moiety, wherein
  —R$^4$—R$^5$— is —O—(CH$_2$)$_n$—O— wherein n is 1 or 2;
R$^6$ is hydrogen,
  C$_{1-6}$-alkyl, optionally substituted by CN or OH,
  —(C$_{1-6}$-alkylene)-NR$^g$R$^h$,
    wherein R$^g$ and R$^h$ are each independently selected from
      hydrogen, and C$_{1-6}$-alkyl, or wherein
      R$^g$ and R$^h$ together with the nitrogen to which they are bound form a five or six membered heterocycle comprising one or two heteroatoms selected from the group of nitrogen, oxygen and sulfur,
  —(C$_{1-6}$-alkylene)-C(O)—NR$^i$R$^j$,
    wherein R$^i$ and R$^j$ are each independently
      hydrogen,
      C$_{1-6}$-alkyl,
      —(C$_{1-6}$-alkylene)-NR$^k$R$^l$,
        wherein R$^k$ and R$^l$ are each independently hydrogen or C$_{1-6}$-alkyl;
    or R$^i$ and R$^j$ together with the nitrogen to which they are bound form a five or six membered heterocycle comprising one or two heteroatoms selected from the group of nitrogen, oxygen and sulfur,
  —O-benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
  nitro,
  halo,
  cyano,
  C$_{1-6}$-alkoxy,
  halo-C$_{1-6}$-alkoxy,
  halo-C$_{1-6}$-alkyl,
  —(C$_{1-6}$-alkylene)-C(O)R$^f$; wherein
    R$^f$ is selected from
      hydrogen,
      C$_{1-6}$-alkyl,
      C$_{1-6}$-alkoxy, and
      phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
  phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
  —(C$_{1-3}$-alkylene)-R$^m$, wherein R$^m$ is phenyl, a 5- to 6-membered heteroaryl, 4- to 6-membered heterocycloalkyl or 3 to 6-membered cycloalkyl, each optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
or R$^5$ and R$^6$ are bound together to form a ring with the benzo moiety, wherein
  —R$^5$—R$^6$ is —O—(CH$_2$)$_n$—C(O)—,
    —C(O)—(CH$_2$)$_n$—O—, or
    —O—(CH$_2$)$_n$—O— wherein n is 1 or 2,
R$^7$ is hydrogen or C$_{1-6}$-alkyl;
R$^8$, R$^9$, R$^{10}$, and R$^{11}$ are each independently hydrogen, halo, C$_{1-6}$-alkyl or halo-C$_{1-6}$-alkyl.

The invention further encompasses an embodiment with the compound of formula (I), wherein
X is O or CH$_2$;
R$^1$ is hydrogen, or C$_{1-6}$-alkyl, optionally substituted by CN or OH;
R$^2$ is hydrogen or C$_{1-6}$-alkyl;
R$^3$ is hydrogen;
R$^4$ is hydrogen,
  halo,
  C$_{1-6}$-alkyl, or
  C$_{1-6}$-alkoxy;
R$^5$ is hydrogen or halo;
or R$^4$ and R$^5$ are bound together to form a ring with the benzo moiety, wherein
  —R$^4$—R$^5$— is —O—(CH$_2$)$_n$—O— wherein n is 1 or 2,
R$^6$ is hydrogen or C$_{1-6}$-alkyl, optionally substituted by CN or OH;
R$^7$ is hydrogen or C$_{1-6}$-alkyl;
R$^8$, R$^9$, R$^{10}$, and R$^{11}$ are each independently hydrogen or halo.

The invention further encompasses an embodiment with the compound of formula (Ia), wherein
X is O;
R$^1$ is hydrogen, or C$_{1-6}$-alkyl, optionally substituted by CN or OH;
R$^2$ is hydrogen or C$_{1-6}$-alkyl;
R$^3$ is hydrogen;
R$^4$ is hydrogen, halo, or C$_{1-6}$-alkyl;
R$^5$ is hydrogen or halo;
R$^6$ is hydrogen or C$_{1-6}$-alkyl, optionally substituted by CN or OH;
R$^7$ is hydrogen;
R$^8$, R$^9$, R$^{10}$, and R$^{11}$ are each independently hydrogen.

The invention further encompasses an embodiment with the compound of formula (Ib), wherein
X is CH$_2$;
R$^1$ is hydrogen, or C$_{1-6}$-alkyl, optionally substituted by CN or OH;
R$^2$ is hydrogen or C$_{1-6}$-alkyl;
R$^3$ is hydrogen;
R$^4$ is hydrogen, halo, or C$_{1-6}$-alkoxy;
R$^5$ is hydrogen;
or R$^4$ and R$^5$ are bound together to form a ring with the benzo moiety, wherein
  —R$^4$—R$^5$— is —O—(CH$_2$)$_n$—O— wherein n is 1 or 2,
R$^6$ is hydrogen;
R$^7$ is hydrogen;
R$^8$, R$^9$, R$^{10}$, and R$^{11}$ are each independently hydrogen or halo.

Preferred compounds of the invention are those shown in the examples.

More preferred compounds of formula Ia:
1'-[(5-chloro-1-methyl-1H-indol-2-yl)carbonyl]spiro[3,1-benzoxazine-4,4'-piperidin]-2(1H)-one,
{2-[(2-oxo-1,2-dihydro-1'H-spiro[3,1-benzoxazine-4,4'-piperidin]-1'-yl)carbonyl]-1H-indol-1-yl}acetonitrile, and
{5-chloro-2-[(2-oxo-1,2-dihydro-1'H-spiro[3,1-benzoxazine-4,4'-piperidin]-1'-yl)carbonyl]-1H-indol-1-yl}acetonitrile.

More preferred compound of formula Ib:
{2-[(6'-bromo-2'-oxo-2',3'-dihydro-1H,1'H-spiro[piperidine-4,4'-quinolin]-1-yl)carbonyl]-5-chloro-1H-indol-1-yl}acetonitrile.

The invention also encompasses the compounds of formula (I) for a use in the prevention or treatment of dysmenorrhea, hypertension, chronic heart failure, inappropriate secretion of vasopressin, liver cirrhosis, nephrotic syndrome, obsessive compulsive disorder, anxiety and depressive disorders.

The invention also encompasses a pharmaceutical composition comprising a compound of formula (I) which pharmaceutical composition is useful against dysmenorrhea, hypertension, chronic heart failure, inappropriate secretion of vasopressin, liver cirrhosis, nephrotic syndrome, obsessive compulsive disorder, anxiety and depressive disorders. The pharmaceutical composition may further comprise at least one pharmaceutically acceptable excipient.

The invention further encompasses the use of a compound of formula (I) for the preparation of a medicament which is useful against dysmenorrhea, hypertension, chronic heart failure, inappropriate secretion of vasopressin, liver cirrhosis, nephrotic syndrome, obsessive compulsive disorder, anxiety and depressive disorders.

In a certain embodiment, the compound of the invention can be manufactured according to a process comprising reacting a compound of formula (II):

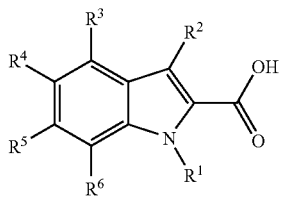

with an amine of formula 1

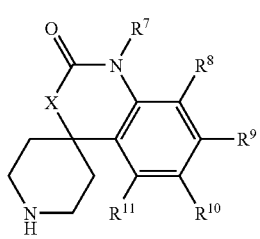

wherein $R^1$ to $R^{11}$ and X are as defined above.

In a certain embodiment, the compound of the invention can be manufactured according to a process comprising reacting a compound of formula (I-1):

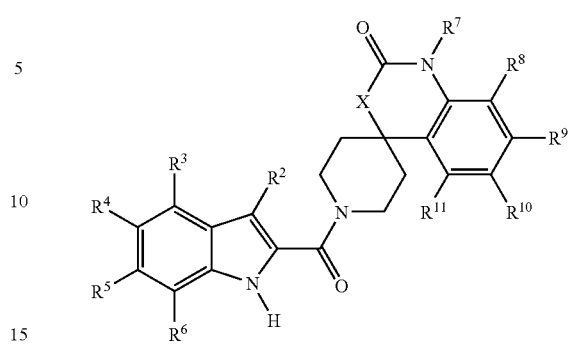

with an electrophile of formula $R^1$-hal, to give a compound of general formula (I) as defined herein above.

The synthesis of compounds of general formula (I) will be described in more detail below and in the examples. The compounds of formula I may be prepared in accordance with the process variants as described above and with the following schemes A-C. The starting materials described in the Example section are either commercially available or are otherwise known or derived from the chemical literature, for instance as cited below, or may be prepared as described in the Examples section.

General scheme A

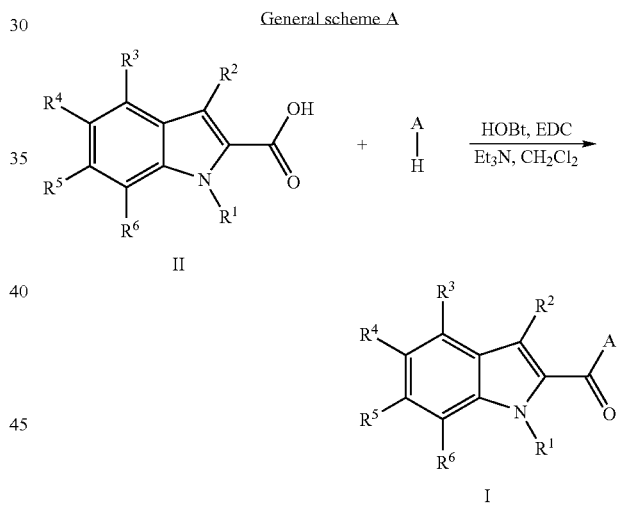

where in A is:

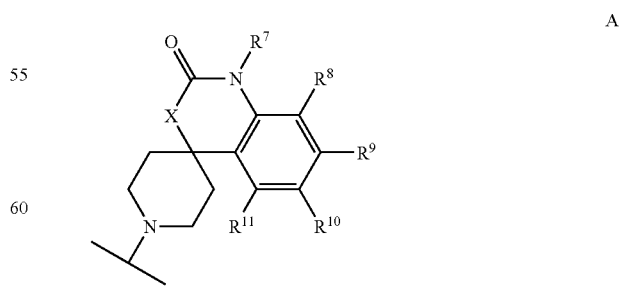

wherein X is O or $CH_3$

Compounds of formula (I) can be prepared via an amide coupling between an indole 2-carboxylic acid (II) and a compound of formula (A-H), wherein A is defined as hereinabove. The usual reagents and protocols known in the art can be used to effect the amide coupling. Indole 2-carboxylic acids (II) are either commercially available or readily prepared using procedures described hereinafter. The compounds of formula (A-H) are either commercially available or prepared using methods known in the art starting from commercially available materials. General scheme A is hereinafter further illustrated with general procedure I.

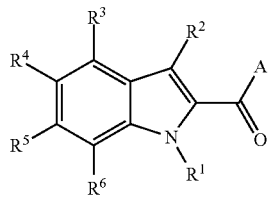

I-2

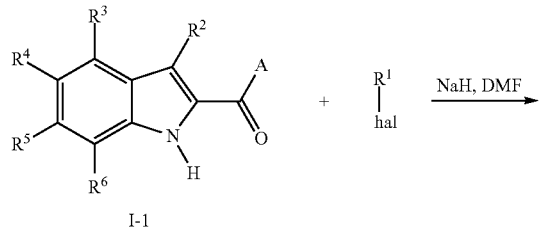

Compounds of formula (I-2) (compounds of formula (I) wherein $R^1$ is different from H), can be prepared by alkylation of the indole derivative of formula (I-1), with an electrophile of formula $R^1$-hal (commercially available, wherein hal is halo, preferably Cl or Br) using standard procedures. Derivatives (I-1) are prepared using the amide coupling as described in the general scheme A.

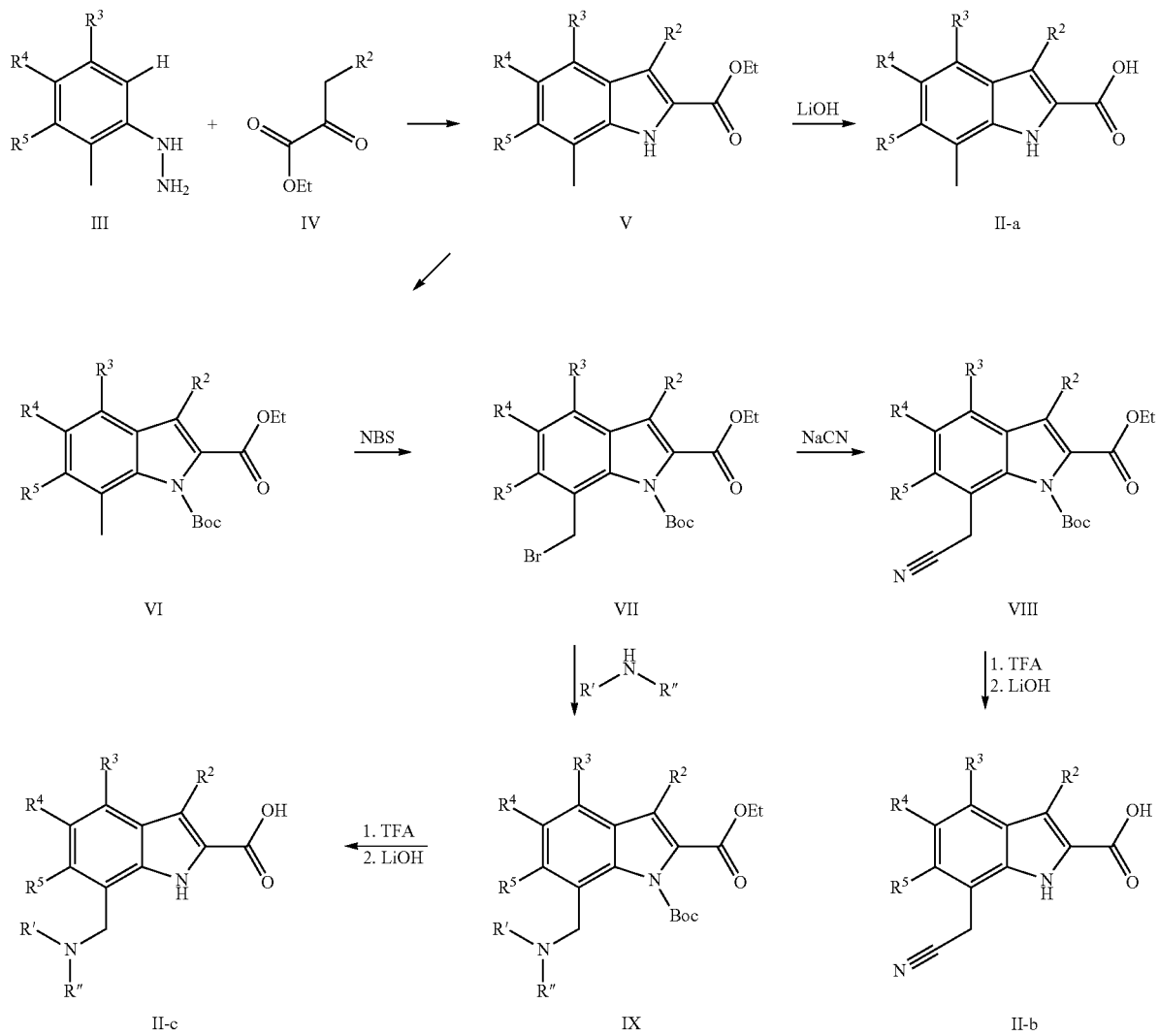

Substituted indole 2-carboxylic acids can be prepared according to the general scheme C. Indoles V are obtained by a Fischer indole synthesis from an aryl hydrazine III and a α-ketoester IV. Saponification gives an acid of formula II-a. Alternatively, Boc protection of the indole nitrogen gives VI. Selective bromination of the methyl group in the 7-position of the indole using NBS affords VII. Subsequent nucleophilic substitution of 7-bromomethyl indole intermediate VII with NaCN or a secondary amine yields intermediates VIII and IX, respectively. After N-deprotection and saponification of the ester moiety, the corresponding carboxylics acids II-b and II-c are obtained.

Abbreviations used:
NBS=N-Bromosuccinimide
Boc=tert-buthoxycarbonyl
EDC=N-(3-dimethylaminopropyl)-N'-ethyl-carbodiimide hydrochloride
HOBt=1-hydroxybenzotriazole
DMF=N,N-dimethylformamide
DMSO=dimethylsulfoxide
DMAP=4-dimethylaminopyridine
TFA=trifluoroacetic acid

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation was centrifuged 20 min at 500 g at 4° C., the pellet was discarded and the supernatant centrifuged 1 hour at 43'000 g at 4° C. (19'000 rpm). The pellet was resuspended in 12.5 ml Lysis buffer+12.5 ml Sucrose 20% and homogenized using a Polytron for 1-2 min. The protein concentration was determined by the Bradford method and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts were subtracted from each well and data was normalized to the maximum specific binding set at 100%. To calculate an IC 50 the curve was fitted using a non-linear regression model (XLfit) and the Ki was calculated using the Cheng-Prussoff equation.

| Ex. | pKi (hV1a) |
|---|---|
| 7 | 7.325 |
| 14 | 7.525 |
| 15 | 7.22 |
| 16 | 7.975 |

The present invention also provides pharmaceutical compositions containing compounds of formula I and/or their pharmaceutically acceptable acid addition salts. Such compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

Example A

Tablets of the following composition can be manufactured in the usual manner:

|  | mg/tablet |
|---|---|
| Active substance | 5 |
| Lactose | 45 |
| Corn starch | 15 |
| Macrocrystalline cellulose | 34 |
| Magnesium stearate | 1 |
| Tablet weight | 100 |

Example B

Capsules of the following composition can be manufactured:

|                      | mg/capsule |
|----------------------|------------|
| Active substance     | 10         |
| Lactose              | 155        |
| Corn starch          | 30         |
| Talc                 | 5          |
| Capsule fill weight  | 200        |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

Example C

Suppositories of the following composition can be manufactured:

|                  | mg/supp. |
|------------------|----------|
| Active substance | 15       |
| Suppository mass | 1285     |
| Total            | 1300     |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool; the suppositories then can be removed from the moulds and packed individually in wax paper or metal foil.

In the following, the synthesis of compounds of formula (I) is further exemplified:

The compounds of formula I may be prepared in accordance with the process variants as described above. The starting materials described in the Example section are either commercially available or are otherwise known or derived from the chemical literature, for instance as cited below, or may be prepared as described in the Examples section.

EXAMPLES

General Procedure I

Amide Coupling

To a 0.1 M stirred solution of an indole-2-carboxylic acid derivative of type (II) in $CH_2Cl_2$ are added EDC (1.3 eq), HOBt (1.3 eq), $Et_3N$ (1.3 eq) and the amine derivative (A-H, as defined above, 1 eq). The mixture is stirred overnight at room temperature and then poured onto water and extracted with $CH_2Cl_2$. The combined organic phases are dried over $Na_2SO_4$ and concentrated in vacuo. Flash chromatography or preparative HPLC affords a compound of formula (I).

General Procedure II

Alkylation

To a 0.1 M stirred solution of a derivative of general formula (I-1) in DMF is added NaH (60% in oil, 2.1 eq.). After stirring the mixture at room temperature for 30 min. the electrophilic reactant $R^1$-hal (1.1 eq.) is added. The mixture is stirred an additional 14 hours at 60° C. and then poured onto water and extracted with ethyl acetate. The combined organic phases are dried over $Na_2SO_4$ and concentrated in vacuo. Purification by preparative HPLC affords the corresponding derivatives of general formula (I-2).

Example 1

6'-Bromo-1-[(5-methoxy-3-methyl-1H-indol-2-yl)carbonyl]-1'H-spiro[piperidine-4,4'-quinolin]-2'(3'H)-one

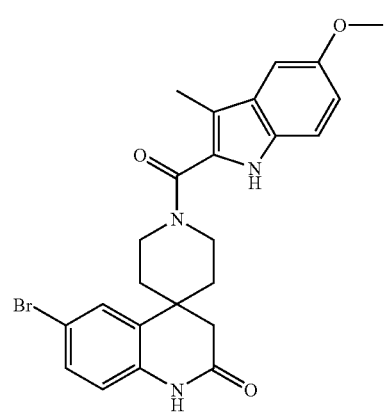

Amide coupling according to general procedure I:
Amine: 6'-Bromo-1'H-spiro[piperidine-4,4'-quinolin]-2'(3'H)-one (prepared herein),
Acid: 5-Methoxy-3-methyl-1H-indole-2-carboxylic acid,
ES-MS m/e (%): 482.4 (M+H$^+$).

6'-Bromo-1'H-spiro[piperidine-4,4'-quinolin]-2'(3'H)-one (Scheme 1)

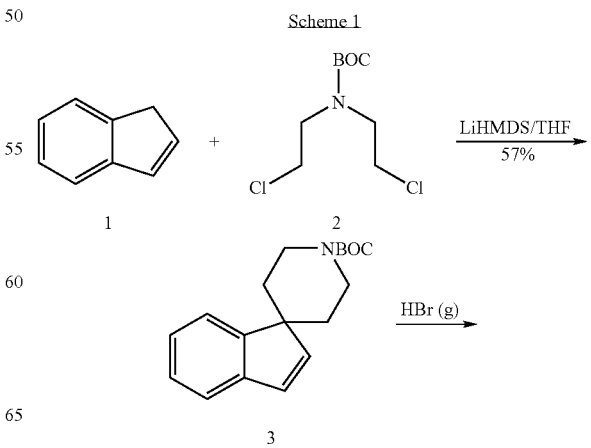

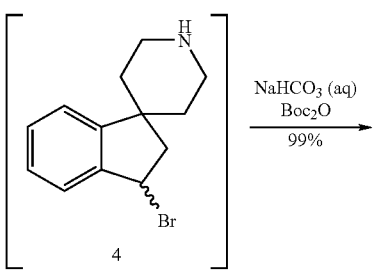

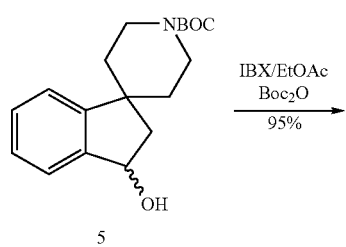

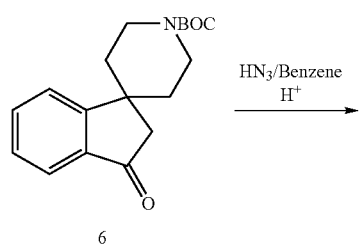

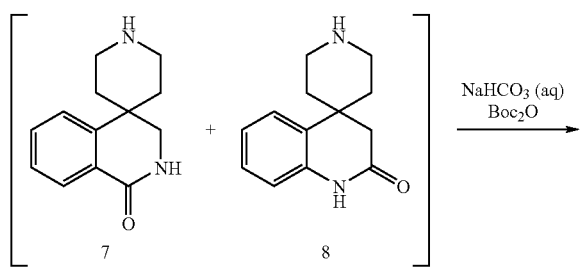

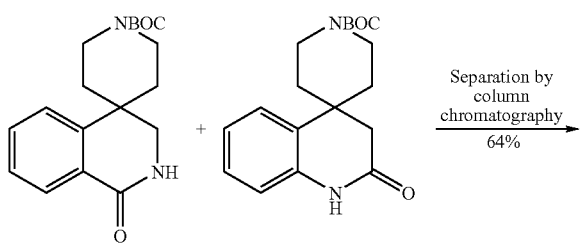

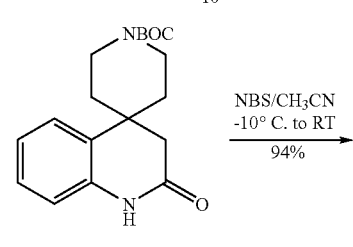

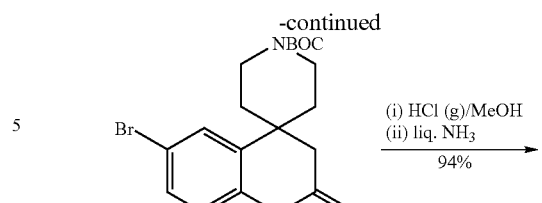

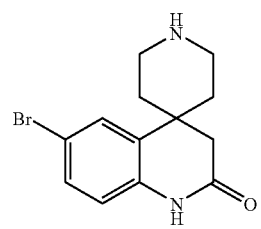

1'-(tert-Butyloxycarbonyl)spiro(indene-1,4'-piperidine) 3

To a solution of indene 1 (34.6 g, 298 mmol) in dry THF (40 mL) maintained under a nitrogen blanket was added lithium bis(trimethylsilyl)amide (596 mL of a 1.0 M solution in THF; 596 mmol) over 30 min. The mixture was stirred in the cold for 30 min and then transferred by a cannula to a solution of N,N-bis(2-chloroethyl)-tert-butyl carbamate 2 (68 g, 281 mmol) in dry THF (40 mL), and stirred in an ice bath. The mixture was stirred for 2 hours in the cold and for 30 min at ambient temperature under nitrogen and then evaporated in vacuo to a foam. Methylene chloride was added and the resulting reaction mixture was chromatographed on silica (1:20 ethyl acetate-hexane). The product fractions were evaporated to dryness in vacuo to give (49 g, 57%) of 1'-(tert-butyloxycarbonyl)spiro(indene-1,4'-piperidine) 3 as a white solid, mp 128° C. IR (KBr) 3435, 2964, 2856, 1679, 1427, 1165 cm-1; 1H NMR (CDCl3, 400 MHz) δ 1.26 (br d, J=13.4 Hz, 2H), 1.43 (s, 9H), 1.93 (dt, J=12.9, 4.5 Hz, 2H), 3.04 (dt, J=13.0, 2.7 Hz, 2H), 4.11 (br d, J=13.5 Hz, 2H), 6.71 (d, J=5.7 Hz, 1H), 6.77 (d, J=5.7 Hz, 1H), 7.11-7.19 (m, 2H), 7.23-7.26 (m, 2H); 13C NMR (CDCl3, 100 MHz) δ 28.47, 33.39, 42.48, 52.03, 79.56, 121.45, 121.65, 125.30, 126.98, 130.25, 140.32, 142.73, 151.65, 155.01; GC MS (EI) m/z 285.

1'-(tert-Butyloxycarbonyl)spiro(indan-1-ol,4'-piperidine) 5

To a stirring solution of 3 (20 g, 70.2 mmol) in dry methylene chloride (450 mL) was passed gaseous HBr for 12 hours. The reaction mixture was carefully neutralized with saturated sodium bicarbonate solution (150 mL). The aqueous part was separated out and the organic part back extracted with saturated sodium bicarbonate (2×50 mL). To the aqueous extract and the combined washings was added 14.7 g of solid sodium bicarbonate, 400 mL of methylene chloride followed by 15.4 g (70.2 mmol) of di-tert-butyl pyrocarbonate. The reaction mixture was stirred at ambient temperature for 3 hours. The organic layer was separated out and the aqueous part was washed successively with methylene chloride (3×50 mL), dried and concentrated in vacuo to provide a foaming liquid which was chromatographed on silica (3:7 ethyl acetate-hexane followed by 1:1 ethyl acetate-hexane) to provide 1'-(tert-butyloxycarbonyl)spiro(indan-1-ol, 4'-piperidine) 5 (21 g, 99%) as a viscous liquid. IR (film) 3401, 2925, 2347, 1691, 1669, 1425, 1365, 1166 cm-1; 1H NMR (CDCl3, 400 MHz) δ 1.37 (dd, J=13.4, 2.0 Hz, 1H), 1.49 (s, 9H), 1.62 (dd, J=13.2, 1.9 Hz, 1H), 1.73 (dt, J=13.0, 4.4 Hz, 1H), 1.87-1.96 (m, 2H), 2.49 (dd, J=13.4, 7.1 Hz, 1H), 2.62 (br s, 1H), 2.92 (tt, J=11.7, 2.9 Hz, 2H), 4.09 (d, J=11 Hz, 2H), 5.25 (t, J=12.2 Hz, 1H), 7.18 (d, J=7.4 Hz, 1H), 7.25-7.33 (m, 2H), 7.41 (d, J=7.09 Hz, 1H); 13C NMR (CDCl3, 100 MHz) δ 28.39, 37.04, 38.04, 41.21, 41.37, 44.70, 44.94, 73.98, 79.52, 122.59, 124.43, 127.48, 128.64, 143.96, 150.10, 154.90; MS (EI) m/z 303.

1'-(tert-Butyloxycarbonyl)-spiro-(indan-1-one, 4'-piperidine) 6

A stirring solution of 5 (20 g, 66 mmol) in ethyl acetate (300 mL) was treated with o-iodoxybenzoic acid (IBX) (37 g, 132 mmol) and was heated at 80° C. for 12 hours. The reaction mixture was brought to room temperature and then filtered under pump. The residue was thoroughly washed with ethylacetate (3×100 mL). The filtrate with the combined washings were concentrated under vacuo to provide a solid residue which was chromatographed over silica (1:10 ethyl acetate-hexane followed by 1:3 ethyl acetate-hexane) to provide 1'-(tert-butyloxycarbonyl)-spiro-(indanl-one,4'-piperidine) 6 (19.5 g, 98%) as a white solid, mp 121° C. IR (KBr) 3388, 2980, 2917, 2847, 1704, 1688, 1603, 1418, 1364, 1278, 1160 cm-1; 1H NMR (CDCl3, 400 MHz) δ 1.46 (s, 9H), 1.49 (m, 2H), 1.95 (dt, J=13.2, 4.6 Hz, 2H), 2.60 (s, 2H), 2.83 (dt, J=13.3, 2.5 Hz, 2H), 4.19 (td, J=13.7, 4.3 Hz, 2H), 7.38 (dt, J=7.1, 0.8 Hz, 1H), 7.46 (d, J=7.8 Hz, 1H), 7.61 (td, J=7.7, 1.2 Hz, 1H), 7.70 (dt, J=7.4, 0.9 Hz, 1H). 13C NMR (CDCl3, 100 MHz) δ 28.38, 37.52, 41.47, 41.58, 46.84, 79.73, 123.62, 123.87, 128.03, 135.09, 135.61, 154.75, 162.02; GC-MS (EI) m/z 301.

1'-(tert-Butyloxycarbonyl)spiro(tetrahydro quinol-2-one)-4'-piperidine 10 and 1'-(tert-butyloxycarbonyl) spiro(tetrahydro isoquinol-1-one)-4'-piperidine 9

To a cooled solution of 6 (10 g, 33 mmol) in dry benzene (40 mL), concentrated sulphuric acid was added with stirring. The reaction mixture was thereafter maintained at 40° C. under stirring followed by dropwise addition of a freshly prepared solution of hydrazoic acid (2.84 g, 66 mmol) in benzene [A paste is prepared from 4.26 g of sodium azide, 4.26 mL of water and 56.8 mL of benzene is added. The mixture is cooled to 0° C. and 1.18 mL of concentrated sulfuric acid is added dropwise with control of temperature from 0-5° C. The organic layer (a solution of hydrazoic acid in benzene) is separated, dried over sodium sulphate and used for the reaction. When the effervescence had ceased, the benzene layer was carefully decanted off and the residue washed with benzene (2×10 mL). Traces of benzene were removed under vacuo and the residue dissolved in 70 mL of water followed by neutralization with liquor ammonia (10 mL). The reaction mixture was then treated with 7 g of solid sodium bicarbonate, di-tert-butyl pyrocarbonate (7.2 g) in 250 mL of methylene chloride and stirred for 2 hours at ambient temperature. The organic layer was separated out and the aqueous part was washed with methylene chloride (2×50 mL). The combined organic extract and washings were washed with brine, dried (anhydrous Na2SO4), concentrated under vacuo to provide a foamy material which was chromatographed over silica (1:3 ethyl acetate-hexane followed by 1:1 ethyl acetate hexane) to provide 1'-(tert-butyloxycarbonyl)spiro(tetrahydro quinol-2-one)-4'-piperidine 10 (6.7 g, 64%) as a creamish white solid, mp 198° C. IR (KBr) 3205, 3080, 2978, 1681, 1591, 1487, 1432, 1381, 1252, 1174 cm-1; 1H NMR (CDCl3, 400 MHz) δ 1.46 (s, 9H), 1.67 (d, J=12.2 Hz, 2H), 1.88 (br t, J=10.1 Hz, 2H), 2.70 (s, 2H), 3.08 (t, J=12.2 Hz, 2H), 4.00 (br d, J=9.2 Hz, 2H), 6.83 (dd, J=7.8, 1.1 Hz, 1H), 7.06 (dt, J=7.6, 1.2 Hz, 1H), 7.20 (dt, J=7.6, 1.2 Hz, 1H), 7.29 (dd, J=7.3, 0.9 Hz, 1H), 8.75 (br s, 1H); 13C NMR (CDCl3, 100 MHz) δ 28.39, 33.69, 35.32, 37.75, 39.31, 79.73, 116.38, 123.82, 124.00, 127.89, 131.25, 136.24, 154.76, 170.67; GC-MS (EI) m/z 316.

1'-(tert-Butyloxycarbonyl)spiro(tetrahydro isoquinol-1-one)-4'-piperidine 9

This was compound was eluted with 1:1 ethyl acetate-hexane. (3.8 g, 36%) mp 182 0C; IR (KBr) 3337, 3232, 2867, 1692, 1679, 1635, 1603, 1415, 1165 cm-1; 1H NMR (400 MHz, CDCl3) δ 1.47 (s, 9H), 1.78 (m, 2H), 1.94 (br s, 2H), 2.99 (t, J=12.9 Hz, 2H), 3.57 (br d, J=1.7 Hz, 2H), 4.01 (br d, J=15.6 Hz, 2H), 6.24 (br s, 1H), 7.38 (m, 2H), 7.53 (m, 1H), 8.10 (dd, J=7.9, 1.6 Hz, 1H); 13C NMR (CDCl3, 100 MHz) δ 28.35, 29.59, 32.59, 35.63, 44.79, 79.73, 122.99, 127.04, 127.83, 128.46, 132.83, 146.36, 154.74; GC-MS (EI) m/z: (M−100).

6-Bromo-1'-(tert-butyloxycarbonyl)spiro(tetrahydro quinol-2-one)-4'-piperidine 11

A solution of 10 (10 g, 31.6 mmol) in dry acetonitrile (250 mL) was cooled to −10° C., and N-bromosuccinimide (5.62 g, 31.6 mmol) was added portion wise with stirring. The reaction mixture was stirred for 1 h at −10 C, 2 h at 0° C. and finally at ambient temperature for 24 h. The solvent was removed and the residue dissolved in methylene chloride (500 mL), organic extract washed with brine-water (1:1) (3×50 mL), dried (anhydrous Na2SO4), concentrated in vacuo to provide a creamish white solid which was chromatographed over silica (1:3 ethyl acetate-hexane followed by 1:1 ethyl-acetate hexane) to give 6-bromo-1'-(tert-butyloxycarbonyl)spiro (tetrahydro quinol-2-one)-4'-piperidine 11 (11.8 g, 94%) as a white solid of mp 226° C. IR (KBr) 3178, 3083, 2923, 1686, 1586, 1491, 1432, 1380, 1255, 1171 cm-1; 1H NMR (CDCl3, 400 MHz) δ 1.46 (s, 9H), 1.65 (m, 2H), 1.85 (br t, 2H), 2.69 (br s, 2H), 3.05 (br t, 2H), 4.02 (br s, 2H), 6.72 (d, J=8.4 Hz, 1H), 7.32 (dd, J=8.4, 2.0 Hz, 1H), 7.41 (d, J=2.0 Hz, 1H), 8.75 (s, 1H); 13C NMR (100 MHz, CDCl3) δ 28.38, 33.56, 35.58, 37.31, 79.88, 116.46, 117.93, 127.31, 130.76, 133.33, 135.39, 154.62, 170.58; GC-MS (EI) m/z (M−100) 294.

6'-Bromo-1'H-spiro[piperidine-4,4'-quinolin]-2' (3'H)-one 12

To a stirring solution of 11 (10 g, 25.3 mmol) in 750 mL of methanol, dry HCl was passed for 10 hrs and the stirring was continued for overnight. The reaction mixture was neutralized with liquor ammonia (75 mL) under ice-cold condition. Methanol and excess ammonia were removed under vacuo and the residue dissolved in methylene chloride (500 mL) followed by the addition of 25 mL of liquor ammonia to dissolve the remaining solid. The organic layer was separated out and the aqueous part washed extracted with methylene chloride (3×150 mL), dried (anhydrous Na2SO4), concentrated under vacuo to provide 6-bromo-spiro(tetrahydro quilon-2-one)-4'-piperidine 12 as a creamish white solid (7.0 g, 94%) of mp 218 0C. IR (KBr) 3434, 3318, 3180, 2823, 1668, 1600, 1483, 1389 cm-1; 1H NMR (d6-DMSO, 400 MHz) δ 1.45 (d, J=12.7 Hz, 2H), 1.71 (dt, J=12.3, 4.8 Hz, 2H); 2.57 (br s, 2H), 2.68-2.78 (m, 4H), 6.83 (d, J=8.4 Hz, 1H), 7.33 (dd, J=8.4, 1.9 Hz, 1H), 7.41 (br d, J=1.9 Hz, 1H), 10.3 (br s, 1H); 1H NMR ($D_2O$ exchange, d6-DMSO, 400 MHz) δ 1.43 (d, J=12.9 Hz, 2H), 1.71 (dt, J=12.2, 4.8 Hz, 2H), 2.55 (br s, 2H), 2.65-2.76 (m, 4H), 6.82 (d, J=8.4 Hz, 1H), 7.29 (dd, J=8.4, 1.9 Hz, 1H), 7.39 (br d, J=1.9 Hz, 1H); 13C NMR (100 MHz, d6-DMSO) δ 34.14, 35.58, 37.34, 41.06, 114.28, 117.57, 126.75, 129.89, 134.74, 136.56, 168.73; GC-MS (EI) m/z 294.

Example 2

6'-Bromo-1-(5H-[1,3]dioxolo[4,5-f]indol-6-ylcarbonyl)-1'H-spiro[piperidine-4,4'-quinolin]-2'(3'H)-one

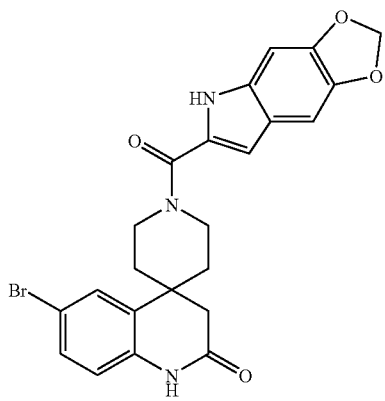

Amide coupling according to general procedure I:
Amine: 6'-Bromo-1'H-spiro[piperidine-4,4'-quinolin]-2'(3'H)-one (prepared herein above),
Acid: 5H-[1,3]Dioxolo[4,5-f]indole-6-carboxylic acid,
ES-MS m/e (%): 482.3 (M+H+).

Example 3

6'-Bromo-1-[(5-methoxy-1H-indol-2-yl)carbonyl]-1'H-spiro[piperidine-4,4'-quinolin]-2'(3'H)-one

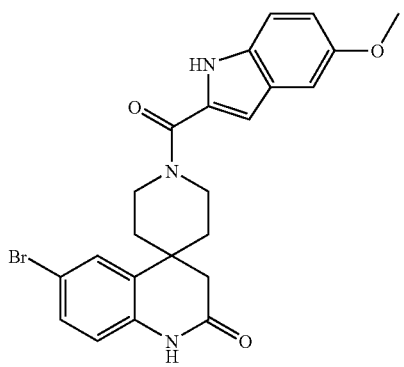

Amide coupling according to general procedure I:
Amine: 6'-Bromo-1'H-spiro[piperidine-4,4'-quinolin]-2'(3'H)-one (prepared herein above),
Acid: 5-Methoxy-1H-indole-2-carboxylic acid,
ES-MS m/e (%): 468.4 (M+H+).

Example 4

6'-Bromo-1-[(5-fluoro-1H-indol-2-yl)carbonyl]-1'H-spiro[piperidine-4,4'-quinolin]-2'(3'H)-one

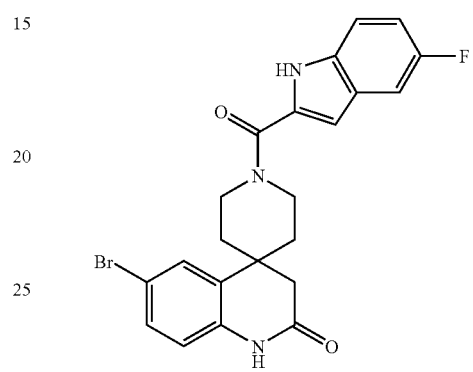

Amide coupling according to general procedure I:
Amine: 6'-Bromo-1'H-spiro[piperidine-4,4'-quinolin]-2'(3'H)-one (prepared herein above),
Acid: 5-Fluoro-1H-indole-2-carboxylic acid,
ES-MS m/e (%): 456.4 (M+H+).

Example 5

6'-Bromo-1-[(5-chloro-1-methyl-1H-indol-2-yl)carbonyl]-1'H-spiro[piperidine-4,4'-quinolin]-2'(3'H)-one

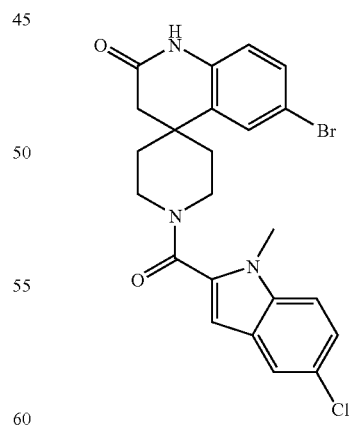

Amide coupling according to general procedure I:
Amine: 6'-Bromo-1'H-spiro[piperidine-4,4'-quinolin]-2'(3'H)-one (prepared herein above),
Acid: 5-Chloro-1-methyl-1H-indole-2-carboxylic acid,
ES-MS m/e (%): 488.3 (M+H+).

Example 6

{2-[(6'-Bromo-2'-oxo-2',3'-dihydro-1H, 1'H-spiro[piperidine-4,4'-quinolin]-1-yl)carbonyl]-1H-indol-1-yl}acetonitrile

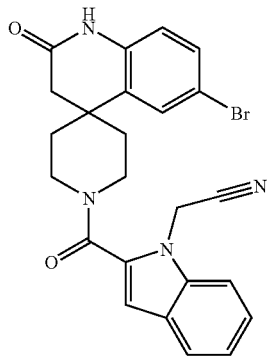

Amide coupling according to general procedure I:

Amine: 6'-Bromo-1'H-spiro[piperidine-4,4'-quinolin]-2'(3'H)-one (prepared herein above), Acid: 1-Cyanomethyl-1H-indole-2-carboxylic acid (prepared herein below), ES-MS m/e (%): 477.4 (M+H$^+$).

Cyanomethyl-1H-indole-2-carboxylic acid

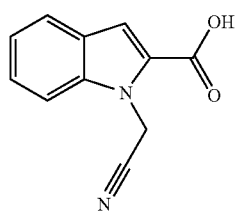

To a solution of 1.0 eq. of 1-cyanomethyl-1H-indole-2-carboxylic acid ethyl ester in a mixture of THF/H$_2$O ((9/1) was added LiOH.H$_2$O (1.0 eq.) and the reaction mixture stirred 6 h at RT, acidified to pH2 and then partially concentrated until precipitation of the crude product which was filtered off and washed with Et$_2$O and then dried to give the desired product as a light yellow solid (70%).

ES-MS m/e (%): 199.0 (M−H$^+$).

Example 7

{2-[(6'-Bromo-2'-oxo-2',3'-dihydro-1H,1'H-spiro[piperidine-4,4'-quinolin]-1-yl)carbonyl]-5-chloro-1H-indol-1-yl}acetonitrile

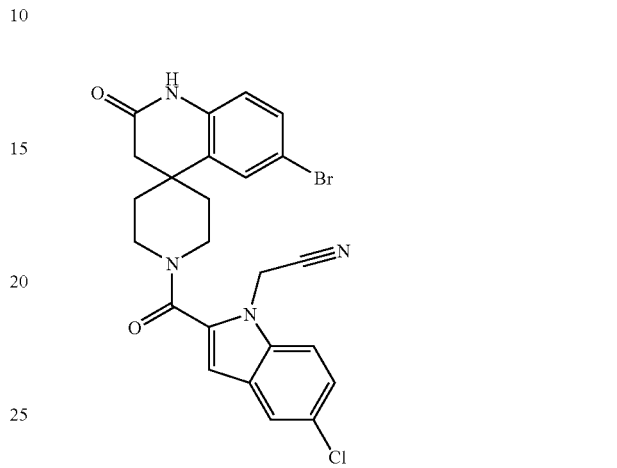

Amide coupling according to general procedure I:

Amine: 6'-Bromo-1'H-spiro[piperidine-4,4'-quinolin]-2'(3'H)-one (prepared herein above), Acid: 5-Chloro-1-cyanomethyl-1H-indole-2-carboxylic acid (prepared herein below), ES-MS m/e (%): 511.0 (M+H$^+$).

5-Chloro-1-cyanomethyl-1H-indole-2-carboxylic acid

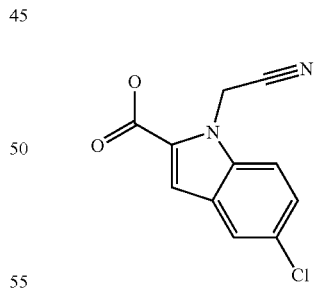

To a solution of 1.0 eq. of 5-chloro-1-cyanomethyl-1H-indole-2-carboxylic acid ethyl ester (CAS 126718-08-9; prepared according to Indian Journal of Chemistry, Section B: Organic Chemistry Including Medicinal Chemistry (1989), 28B(12), 1065-8) in a mixture of THF/H$_2$O ((9/1) was added LiOH.H$_2$O (1.0 eq.) and the reaction mixture stirred 6 h at RT, acidified to pH 2 and then partially concentrated until precipitation of the crude product which was filtered off and washed with Et$_2$O and then dried to give the desired product as a light yellow solid (84%).

Example 8

1-[(5-Chloro-1H-indol-2-yl)carbonyl]-1'H-spiro[piperidine-4,4'-quinolin]-2'(3'H)-one

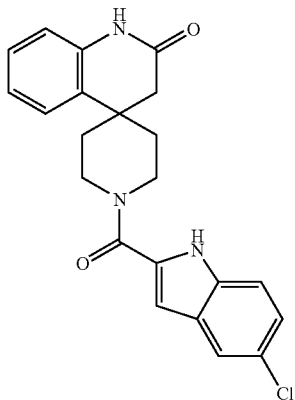

Amide coupling according to general procedure I:
Amine: 1'H-Spiro[piperidine-4,4'-quinolin]-2'(3'H)-one hydrochloride (prepared herein above),
Acid: 5-Chloro-1H-indole-2-carboxylic acid,
ES-MS m/e (%): 394.4 (M+H$^+$).

Example 9

6'-Bromo-1-[(5-chloro-1H-indol-2-yl)carbonyl]-1'H-spiro[piperidine-4,4'-quinolin]-2'(3'H)-one

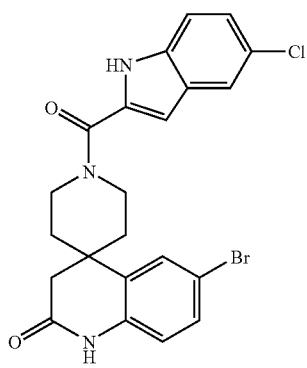

Amide coupling according to general procedure I:
Amine: 6'-Bromo-1'H-spiro[piperidine-4,4'-quinolin]-2'(3'H)-one (prepared herein above),
Acid: 5-Chloro-1H-indole-2-carboxylic acid,
ES-MS m/e (%): 470.3 (M–H$^+$).

Example 10

1'-[(3-Methyl-1H-indol-2-yl)carbonyl]Spiro[3,1-benzoxazine-4,4'-piperidin]-2(1H)-one

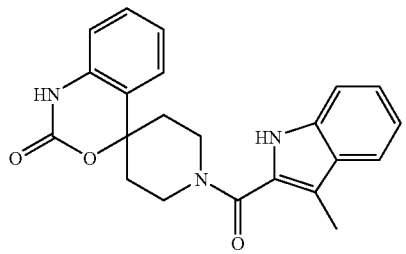

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 3-Methyl-1H-indole-2-carboxylic acid,
ES-MS m/e (%): 374.4 (M–H$^+$).

Example 11

1'-[(7-Methyl-1H-indol-2-yl)carbonyl]Spiro[3,1-benzoxazine-4,4'-piperidin]-2(1H)-one

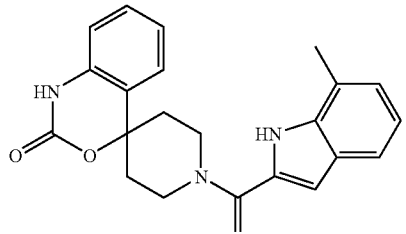

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 7-Methyl-1H-indole-2-carboxylic acid,
ES-MS m/e (%): 376.4 (M+H$^+$).

Example 12

1'-[(6-Chloro-1H-indol-2-yl)carbonyl]spiro[3,1-benzoxazine-4,4'-piperidin]-2(1H)-one

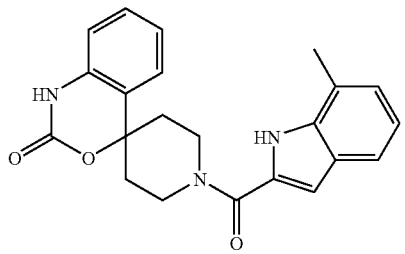

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 6-Chloro-1H-indole-2-carboxylic acid,
ES-MS m/e (%): 396.4 (M+H$^+$).

Example 13

1'-[(5-Methyl-1H-indol-2-yl)carbonyl]spiro[3,1-benzoxazine-4,4'-piperidin]-2(1H)-one

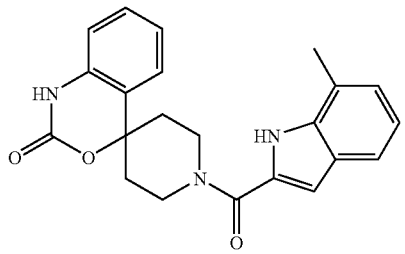

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 5-Methyl-1H-indole-2-carboxylic acid,
ES-MS m/e (%): 376.4 (M+H$^+$).

Example 14

1'-[(5-Chloro-1-methyl-1H-indol-2-yl)carbonyl]spiro[3,1-benzoxazine-4,4'-piperidin]-2(1H)-one

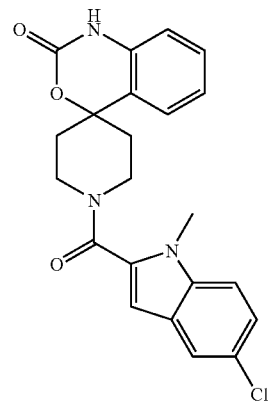

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 5-Chloro-1-methyl-1H-indole-2-carboxylic acid,
ES-MS m/e (%): 410.4 (M+H$^+$).

Example 15

{2-[(2-Oxo-1,2-dihydro-1'H-spiro[3,1-benzoxazine-4,4'-piperidin]-1'-yl)carbonyl]-1H-indol-1-yl}acetonitrile

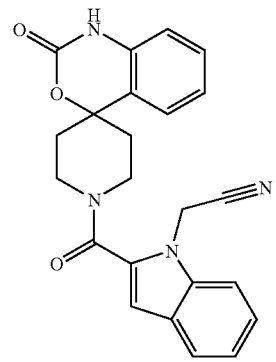

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 1-Cyanomethyl-1H-indole-2-carboxylic acid (prepared herein above),
ES-MS m/e (%): 401.4 (M+H$^+$).

Example 16

{5-Chloro-2-[(2-oxo-1,2-dihydro-1'H-spiro[3,1-benzoxazine-4,4'-piperidin]-1'-yl)carbonyl]-1H-indol-1-yl}acetonitrile

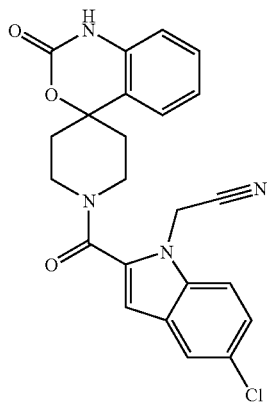

Amide coupling according to general procedure I:
Amine: Spiro[3,1-benzoxazine-4,4'-piperidin]-2(1H)-one (CAS 84060-09-3; described in Chemical & Pharmaceutical Bulletin (1985), 33(3), 1129-39.),
Acid: 5-Chloro-1-cyanomethyl-1H-indole-2-carboxylic acid (prepared herein above),
ES-MS m/e (%): 435.4 (M+H$^+$).

The invention claimed is:
1. A compound of formula (Ib)

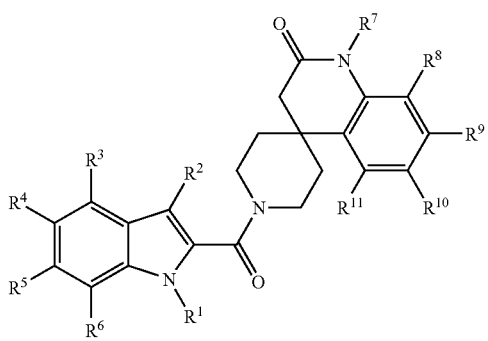

Ib wherein
$R^1$ is hydrogen,
  $C_{1-6}$-alkyl, optionally substituted by CN or OH, or
  —($C_{1-6}$-alkylene)-C(O)—NR$^a$R$^b$;
$R^2$ is hydrogen,
  $C_{1-6}$-alkyl,
  $C_{1-6}$-alkoxy,
  —($C_{1-6}$-alkylene)-NR$^c$R$^d$,
  —($C_{1-6}$-alkylene)-C(O)R$^f$,
  benzyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
  halo, or
  $C_{1-6}$-alkyl;
$R^4$ is hydrogen,
  halo,
  $C_{1-6}$-alkyl,
  halo-$C_{1-6}$-alkyl,
  $C_{1-6}$-alkoxy,
  halo-$C_{1-6}$-alkoxy, or
  —O—$C_{2-10}$-alkenyl;
$R^5$ is hydrogen,
  halo,
  $C_{1-6}$-alkyl, or
  $C_{1-6}$-alkoxy;
$R^6$ is hydrogen,
  $C_{1-6}$-alkyl, optionally substituted by CN or OH,
  —($C_{1-6}$-alkylene)-NR$^g$R$^h$,
  —($C_{1-6}$-alkylene)-C(O)—NR$^i$R$^j$,
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-C(O)R$^f$,
  phenyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
  —($C_{1-3}$-alkylene)-R$^m$,
    wherein R$^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^7$ is hydrogen or $C_{1-6}$-alkyl;
$R^8$, $R^9$, $R^{10}$, and $R^{11}$ are each independently hydrogen, halo, $C_{1-6}$-alkyl, $C_{1-6}$-alkoxy or halo-$C_{1-6}$alkoxy;
$R^a$, $R^b$, $R^i$ and $R^j$ are each independently
  hydrogen,
  $C_{1-6}$-alkyl,
  —($C_{1-6}$-alkylene)-NR$^k$R$^l$;
    wherein R$^k$ and R$^l$ are each independently hydrogen or $C_{1-6}$-alkyl,
$R^c$, $R^d$, $R^g$ and $R^h$ are each independently
  hydrogen,
  $C_{1-6}$-alkyl,
  —C(O)R$^e$, or —S(O)$_2$R$^e$,
    wherein R$^e$ is selected from
      hydrogen,
      $C_{1-6}$-alkyl, and
      phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
R$^f$ is selected from
  hydrogen,
  $C_{1-6}$-alkyl,
  $C_{1-6}$-alkoxy; and
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or a pharmaceutically acceptable salt thereof.
2. The compound of claim 1, wherein
$R^1$ is hydrogen or $C_{1-6}$-alkyl, optionally substituted by CN or OH.

3. The compound of claim 1, wherein
R² is hydrogen,
   $C_{1-6}$-alkyl,
   $C_{1-6}$-alkoxy,
   —($C_{1-6}$-alkylene)-NR$^c$R$^d$,
      wherein R$^c$ and R$^d$ are each independently
         hydrogen,
         —C(O)R$^e$, or —S(O)$_2$R$^e$,
            wherein R$^e$ is selected from
               hydrogen,
               $C_{1-6}$-alkyl, and
               phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
   —($C_{1-6}$-alkylene)-C(O)R$^f$,
      wherein R$^f$ is selected from
         hydrogen,
         $C_{1-6}$-alkoxy, and
         phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
   benzyl, optionally subsitituted by halo, halo-$C_{1-6}$-alkyl, $C_{1-6}$-alkoxy, halo-$C_{1-6}$-alkoxy, nitro, or cyano, or
   phenyl, optionally subsitituted by halo, halo-$C_{1-6}$-alkyl, $C_{1-6}$-alkyl, halo-$C_{1-6}$-alkoxy, nitro, or cyano.

4. The compound of claim 1, wherein R² is hydrogen, or $C_{1-6}$-alkyl.

5. The compound of claim 1, wherein R³ is hydrogen.

6. The compound of claim 1, wherein R⁴ is hydrogen, halo, $C_{1-6}$-alkyl, or $C_{1-6}$-alkoxy.

7. The compound of claim 1, wherein
R⁶ is hydrogen,
   $C_{1-6}$-alkyl, optionally substituted by CN or OH,
   —($C_{1-6}$-alkylene)-NR$^g$R$^h$,
      wherein R$^g$ and R$^h$ are each independently selected from hydrogen and $C_{1-6}$-alkyl;
   —($C_{1-6}$-alkylene)-C(O)—NR$^i$R$^j$,
      wherein R$^i$ and R$^j$ are each independently
         hydrogen,
         $C_{1-6}$-alkyl,
         —($C_{1-6}$-alkylene)-NR$^k$R$^l$,
            wherein R$^k$ and R$^l$ are each independently hydrogen or $C_{1-6}$-alkyl,
   —O-benzyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
   nitro,
   halo,
   cyano,
   $C_{1-6}$-alkoxy,
   halo-$C_{1-6}$-alkoxy,
   halo-$C_{1-6}$-alkyl,
   —($C_{1-6}$-alkylene)-C(O)R$^f$,
      R$^f$ is selected from
         hydrogen,
         $C_{1-6}$-alkyl,
         $C_{1-6}$-alkoxy, and
         phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
   phenyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
   —($C_{1-3}$-alkylene)-R$^m$, wherein R$^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

8. The compound of claim 1, wherein
R⁶ is hydrogen,
   $C_{1-6}$-alkyl, optionally substituted by CN or OH,
   —($C_{1-6}$-alkylene)-NR$^g$R$^h$,
      wherein R$^g$ and R$^h$ are each independently selected from hydrogen and $C_{1-6}$-alkyl;
   —($C_{1-6}$-alkylene)-C(O)—NR$^i$R$^j$,
      wherein R$^i$ and R$^j$ are each independently
         hydrogen,
         $C_{1-6}$-alkyl,
         —($C_{1-6}$-alkylene)-NR$^k$R$^l$,
            wherein R$^k$ and R$^l$ are each independently hydrogen or $C_{1-6}$-alkyl,
   —O-benzyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
   nitro,
   halo,
   cyano,
   $C_{1-6}$-alkoxy,
   halo-$C_{1-6}$-alkoxy,
   halo-$C_{1-6}$-alkyl,
   —($C_{1-6}$-alkylene)-C(O)R$^f$,
      R$^f$ is selected from
         hydrogen,
         $C_{1-6}$-alkyl,
         $C_{1-6}$-alkoxy, and
         phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
   phenyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
   —($C_{1-3}$-alkylene)-R$^m$, wherein R$^m$ is phenyl, a 5- to 6-membered heteroaryl, 4- to 6-membered heterocloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

9. The compound of claim 1, wherein R⁶ is hydrogen or $C_{1-6}$-alkyl, optionally substituted by CN or OH.

10. The compound of claim 1 wherein R⁷ is hydrogen.

11. The compound of claim 1, wherein R⁸, R⁹, R¹⁰ and R¹¹ are independently hydrogen or halo.

12. The compound of claim 1, wherein R⁸, R⁹, R¹⁰ and R¹¹ are each hydrogen.

13. The compound of claim 1, wherein R⁸, R⁹, and R¹¹ are each hydrogen and R¹⁰ is bromine.

14. The compound of claim 1, wherein R⁹ is fluorine and R⁸, R¹⁰ and R¹¹ are each hydrogen.

15. The compound of claim 1, wherein R⁸, R⁹, R¹⁰ and R¹¹ are each independently hydrogen or methyl.

16. The compound of claim 1, wherein R⁸, R⁹, and R¹⁰ are hydrogen and R¹¹ is methyl.

17. The compound of claim 1, which is
{2-[(6'-bromo-2'-oxo-2',3'-dihydro-1H,1'H-spiro[piperidine-4,4'-quinolin]-1-yl)carbonyl]-5-chloro-1H-indol-1-yl}acetonitrile.

18. The compound of claim 1, wherein none of R¹ to R⁶ are hydrogen.

19. The compound of claim 1, wherein none of R¹ to R¹¹ are hydrogen.

20. The compound of claim 1, wherein $R^m$ is a 5- to 6-membered heteroaryl selected from the group consisting of pyridine, pyrimidine, pyrazine, pyridazine, imidazole, pyrazole, oxazole, and isoxazole.

21. The compound of claim 1, wherein $R^m$ is a 4- to 6-membered heterocycloalkyl group selected from the group consisting of pyrrolidine, oxethane, tetrahydropyrane, piperidine, morpholine, and piperazine.

22. The compound of claim 1, wherein
$R^1$ is hydrogen, $C_{1-6}$-alkyl, optionally substituted by CN or OH;
$R^2$ is hydrogen or $C_{1-6}$-alkyl;
$R^3$ is hydrogen;
$R^4$ is hydrogen, halo, or $C_{1-6}$-alkyl;
$R^5$ is hydrogen, or halo;
$R^6$ is hydrogen or $C_{1-6}$-alkyl optionally substituted by CN or OH;
$R^7$ is hydrogen; and
$R^8$, $R^9$, $R^{10}$, and $R^{11}$ are each hydrogen.

23. A pharmaceutical composition comprising a therapeutically effective mount of a compound of formula (Ib)

Ib wherein
$R^1$ is hydrogen,
   $C_{1-6}$-alkyl, optionally substituted by CN or OH, or
   —($C_{1-6}$-alkylene)-C(O)—NR$^a$R$^b$;
$R^2$ is hydrogen,
   $C_{1-6}$-alkyl,
   $C_{1-6}$-alkoxy,
   —($C_{1-6}$-alkylene)-NR$^c$R$^d$,
   —($C_{1-6}$-alkylene)-C(O)R$^f$,
   benzyl, optionally subisitituted by one or more halo, halo-$C_{1-6}$-alkyl, $C_{1-6}$-alkyl, $C_{1-6}$-alkoxy, halo-$C_{1-6}$-alkoxy, nitro, or cyano, or
   phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
   halo, or
   $C_{1-6}$-alkyl;
$R^4$ is hydrogen,
   halo,
   halo-$C_{1-6}$-alkyl,
   $C_{1-6}$-alkoxy,
   halo-$C_{1-6}$-alkoxy, or
   —O—$C_{2-10}$-alkenyl;
$R^5$ is hydrogen,
   halo,
   $C_{1-6}$-alkyl, or
   $C_{1-6}$-alkoxy;
$R^6$ is hydrogen,
   $C_{1-6}$-alkyl, optionally substituted by CN or OH,
   —($C_{1-6}$-alkylene)-NR$^g$R$^h$,
   —($C_{1-6}$-alkylene)-C(O)—NR$^i$R$^j$,
   —O-benzyl, optionally subsitituted by one or more halo, halo-$C_{1-6}$-alkyl,
   $C_{1-6}$-alkyl, $C_{1-6}$-alkoxy, halo-$C_{1-6}$-alkoxy, nitro, or cyano,
   nitro,
   halo,
   cyano,
   $C_{1-6}$-alkoxy,
   halo-$C_{1-6}$-alkoxy,
   halo-$C_{1-6}$-alkyl,
   —($C_{1-6}$-alkylene)-C(O)R$^f$,
   phenyl, optionally subsitituted by one or more halo, halo-$C_{1-6}$-alkyl, $C_{1-6}$-alkyl, $C_{1-6}$-alkoxy, halo-$C_{1-6}$-alkoxy, nitro, or cyano,
   —($C_{1-3}$-alkylene)-R$^m$,
     wherein $R^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^7$ is hydrogen or $C_{1-6}$-alkyl;
$R^8$, $R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$alkoxy;
$R^a$, $R^b$, $R^i$ and $R^j$ are each independently
   hydrogen,
   $C_{1-6}$-alkyl,
   —($C_{1-6}$-alkylene)-NR$^k$R$^l$;
     wherein $R^k$ and $R^l$ are each independently hydrogen or $C_{1-6}$-alkyl,
$R^c$, $R^d$, $R^g$ and $R^h$ are each independently
   hydrogen,
   $C_{1-6}$-alkyl,
   —C(O)R$^e$, or —S(O)$_2$R$^e$,
     wherein $R^e$ is selected from
       hydrogen,
       $C_{1-6}$-alkyl, and
       phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
$R^f$ is selected from
   hydrogen,
   $C_{1-6}$-alkyl,
   $C_{1-6}$-alkoxy; and
   phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or a pharmaceutically acceptable salt thereof and a pharmaceutically acceptable carrier.

* * * * *